(12) United States Patent
Zia et al.

(10) Patent No.: US 9,125,574 B2
(45) Date of Patent: Sep. 8, 2015

(54) SYSTEM AND METHOD FOR ACOUSTIC DETECTION OF CORONARY ARTERY DISEASE AND AUTOMATED EDITING OF HEART SOUND DATA

(71) Applicant: Rutgers, The State University, New Brunswick, NJ (US)

(72) Inventors: Mohammad Zia, North Brunswick, NJ (US); Benjamin Griffel, Highland Park, NJ (US); John Semmlow, New Brunswick, NJ (US)

(73) Assignee: Rutgers, The State University, New Brunswick, NJ (US)

(*) Notice: Subject to any disclaimer, the term of this patent is extended or adjusted under 35 U.S.C. 154(b) by 0 days.

(21) Appl. No.: 14/138,993

(22) Filed: Dec. 23, 2013

(65) Prior Publication Data

US 2014/0180153 A1    Jun. 26, 2014

Related U.S. Application Data

(63) Continuation-in-part of application No. 12/311,168, filed as application No. PCT/US2007/079178 on Sep. 21, 2007, now abandoned.

(60) Provisional application No. 60/846,643, filed on Sep. 22, 2006, provisional application No. 60/846,573, filed on Sep. 22, 2006.

(51) Int. Cl.
*A61B 5/02* (2006.01)
*A61B 7/04* (2006.01)

(52) U.S. Cl.
CPC ............... *A61B 7/04* (2013.01); *A61B 5/02007* (2013.01); *A61B 2562/14* (2013.01); *A61B 2562/168* (2013.01)

(58) Field of Classification Search
CPC .......... A61B 7/04; A61B 5/7203; A61B 7/02
USPC .................................................. 600/528, 508
See application file for complete search history.

(56) References Cited

U.S. PATENT DOCUMENTS

| | | | | |
|---|---|---|---|---|
| 5,036,857 A | * | 8/1991 | Semmlow et al. | 600/528 |
| 5,109,863 A | | 5/1992 | Semmlow et al. | 600/528 |
| 5,492,129 A | * | 2/1996 | Greenberger | 600/528 |
| 5,638,823 A | | 6/1997 | Akay et al. | 600/528 |
| 6,050,950 A | * | 4/2000 | Mohler | 600/485 |
| 2006/0018524 A1 | | 1/2006 | Suzuki et al. | 382/128 |
| 2006/0074315 A1 | | 4/2006 | Liang et al. | 600/450 |
| 2006/0116593 A1 | | 6/2006 | Zhang et al. | 600/512 |

OTHER PUBLICATIONS

Office Communication dated Apr. 13, 2012 from U.S. Appl. No. 12/311,168, filed Dec. 16, 2009.
Office Communication dated Jan. 3, 2013 from U.S. Appl. No. 12/311,168, filed Dec. 16, 2009.

(Continued)

*Primary Examiner* — Amanda Patton
*Assistant Examiner* — Philip Edwards
(74) *Attorney, Agent, or Firm* — Licata & Tyrrell P.C.

(57) ABSTRACT

Systems and methods for acoustic detection of coronary artery disease (CAD) and automated editing of heart sound data are provided.

9 Claims, 14 Drawing Sheets

(56) References Cited

OTHER PUBLICATIONS

International Search Report from PCT/US2007/079178, Apr. 10, 2008.

International Preliminary Report on Patentability from PCT/US2007/079178, Apr. 2, 2009.

\* cited by examiner

SYSTEM AND METHOD FOR ACOUSTIC DETECTION OF CORONARY ARTERY DISEASE AND AUTOMATED EDITING OF HEART SOUND DATA

The present application is a continuation-in-part of U.S. Application Ser. No. 12/311,168, filed Dec. 16, 2009, which is the National Stage of International Application No. PCT/US2007/079178, filed Sep. 21, 2007, which claims the benefit of U.S. Provisional Application Ser. No. 60/846,643, filed Sep. 22, 2006, and U.S. Provisional Application Ser. No. 60/846,573, filed Sep. 22, 2006, the entire disclosures of which are expressly incorporated herein by reference.

This invention was made with government support under Grant No. 1 R41 HL079672 awarded by the National Institutes of Health. The government has certain rights in the invention.

FIELD OF THE INVENTION

The present invention relates to medical diagnostic systems, and more particularly, to a system and method for acoustic detection of coronary artery disease and automated editing of heart sound data.

BACKGROUND OF THE INVENTION

Coronary artery disease (CAD) is a major cause of death in industrialized nations, and approximately 13 million people in the United States are estimated to have the disease. CAD is caused by the thickening and hardening of arterial walls, as well as plaque deposits (including fat, cholesterol, fibers, calcium, and other substances from the blood) accumulated in the arteries. Over time, the plaque deposits narrow the arteries and deprive the heart of oxygen. This can cause blood clots, and in some instances, can completely block arteries, causing blood flow to the heart to stop. Reduced blood flow reduces the oxygen supply to the heart muscles, which can cause chest pain (angina), heart attack, heart failure, or arrhythmias. Often, sudden death results. Thus, there is an urgent need for a non-invasive way to detect and screen for coronary occlusions so that simple, inexpensive treatment plans (including diet and/or drugs) can be expeditiously implemented to reverse the disease before it damages the heart tissue.

To date, the only definitive test for CAD is coronary angiography, a procedure which is invasive, expensive, requires hospitalization, and carries health risks. Newer technologies, such as electron beam Computer Tomography (ebCT), expose the patient to possible health risks from radiation and/or dye contrast agents, are very costly, and require major capital investments and specialized operational staff. Older technologies, such as stress electrocardiology (ECG), expose the patient to moderate risk, remain labor intensive, are still fairly expensive, and have uncomfortably low specificity and sensitivity, especially for women.

In the past, various techniques have been developed for determining the presence of CAD in a patient through analysis of acoustic heart signals taken at one or more locations near the patient's heart. Unfortunately, such techniques analyzed only a very limited range of feature parameters associated with the acoustic signal, and often analyze only a limited range of frequencies of the acoustic signal. Moreover, the presence of noise in the acoustic signal can significantly adversely affect the ability of existing techniques to accurately diagnose CAD in a patient. Finally, clinical studies have shown only modest specificity.

Accordingly, what would be desirable, but has not yet been provided, is a system and method for acoustic detection of coronary heart disease, which address the foregoing limitations of existing detection techniques.

SUMMARY OF THE INVENTION

The present invention relates to systems and methods for acoustic detection of coronary artery disease (CAD) and automated editing of heart sound data.

In one embodiment, the invention comprises a transducer or microphone for acoustically detecting heart signals of a patient, an amplifier for amplifying the detected heart signals, and a computer system which executes detection software for processing the detected heart signals using a plurality of signal detection algorithms which analyze a plurality of feature parameters of the acoustic signal, detecting the presence of CAD from the heart signals, and indicating the presence of CAD. The software provides for automatic detection of a diastolic "window" of the acoustic signal for analysis, and includes automated editing of the sampled acoustic signal to eliminate unwanted artifacts and/or noise in the acoustic signal. The edited signal is then processed by a plurality of signal processing algorithms, including spectral analysis algorithms, time-frequency algorithms, global feature algorithms, kurtosis algorithms, mutual information algorithms, negentropy algorithms, and principal component analysis algorithms, to generate a disease vector. The disease vector is then classified to determine whether CAD is present in the patient. Classification can be accomplished using linear discriminant analysis or a support vector machine (SVM).

The present invention also provides systems and methods for adaptively canceling noise in an acoustic heart signal and/or automatically editing heart sound data. In one embodiment, a first transducer is positioned near a heart and acquires an acoustic heart signal having a noise component. One or more reference transducers or microphones are positioned away from the heart, and acquire noise signals.

In one embodiment, the noise signals detected by a pair of reference transducers are processed by adaptive noise cancellation filters to produce processed noise signals. The processed noise signals are subtracted from the acoustic heart signal to remove noise from the signal. Any remaining noise components in the acoustic heart signal are fed back to the adaptive filters, and the filters adjusted in response to the remaining noise components, to remove the remaining noise components from the acoustic heart signal.

In another embodiment, a reference microphone is placed on the right abdomen to capture both external and internal noise at the same time the transducer or active microphone positioned near the heart records the heart sounds. Signals from the reference microphone, in conjunction with an advanced signal processing algorithm identify segments of noise and automatically remove them from the signals recorded by the active microphone.

BRIEF DESCRIPTION OF THE DRAWINGS

These and other important objects and features of the invention will be apparent from the following Detailed Description of the Invention, taken in connection with the accompanying drawings, in which.

DETAILED DESCRIPTION OF THE INVENTION

The present invention relates to systems and methods for acoustic detection of coronary artery disease (CAD) and/or automated editing of heart sound data.

In one embodiment, of the present invention, the system includes a transducer for acoustically detecting heart signals of a patient and a computer system which executes detection software for processing the detected heart signals to identify the presence of CAD from the heart signals. The software automatically detects a diastolic "window" of the acoustic signal for analysis, and automatically edits the sampled acoustic signal to eliminate unwanted artifacts and/or noise in the acoustic signal. The edited signal is then processed by a plurality of signal processing algorithms, to including spectral analysis algorithms, time-frequency algorithms, global feature algorithms, kurtosis algorithms, mutual information algorithms, negentropy algorithms, and principal component analysis algorithms, to generate a disease vector. The disease vector is then classified to determine whether CAD is present in the patient. Classification can be accomplished using linear discriminant analysis or a support vector machine (SVM).

Figure 1:
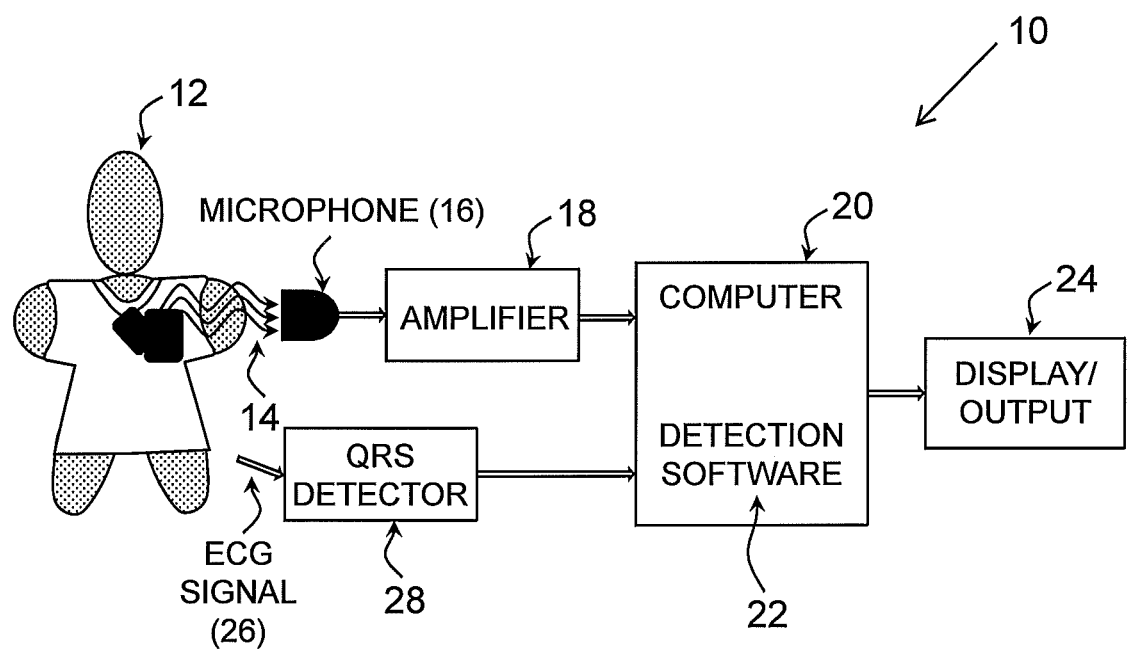
FIG. 1 is diagram showing the system of the present invention for acoustic detection of coronary artery disease.

FIG. 1 is diagram showing an embodiment of a system of the present invention, indicated generally at 10, for acoustic detection of coronary artery disease (CAD). The system 10 allows for the acoustic detection of CAD in a patient 12, and includes a transducer 16 for acoustically detecting heart signals 14 from the patient's heart. An amplifier 18 amplifies the detected heart signals, and transmits the amplified signals to a computer 20. The amplifier 18 could also filter the heart signals so as to remove aliasing effects. The computer 20 includes detection software 22 for analyzing the detected heart signals and indicating the presence or absence of CAD via a display or output 24. Optionally, a QRS detector 28 could be provided for detecting the R-wave of the electrocardiogram (ECG) 26, which could be transmitted to the computer 20 to provide additional timing information. Preferably, the acoustic heart signals amplified by the amplifier 18 are converted to digital form using an analog-to-digital converter, which could be provided within the computer 20 or as part of the amplifier 18. It should be noted that the computer 20 and display 24 could be provided in a variety of forms, such as a personal computer, a workstation, or a handheld computing device (e.g., a personal digital assistant (PDA), pocket computer, etc.) which can be easily transported to a location of the patient 12 for diagnostic use. It is also conceivable that the computer 20 could be substituted with a microcontroller or microprocessor programmed to execute the detection software 22, which could be stored in non-volatile memory associated with the microcontroller or microprocessor. The cardiac microphone 16 could comprise any suitable cardiac microphone or transducer, such as those shown in FIGS. 2-4 and described below, having sufficient sensitivity to allow for the detection of cardiac stenosis from acoustic heart signals.

Figure 2:
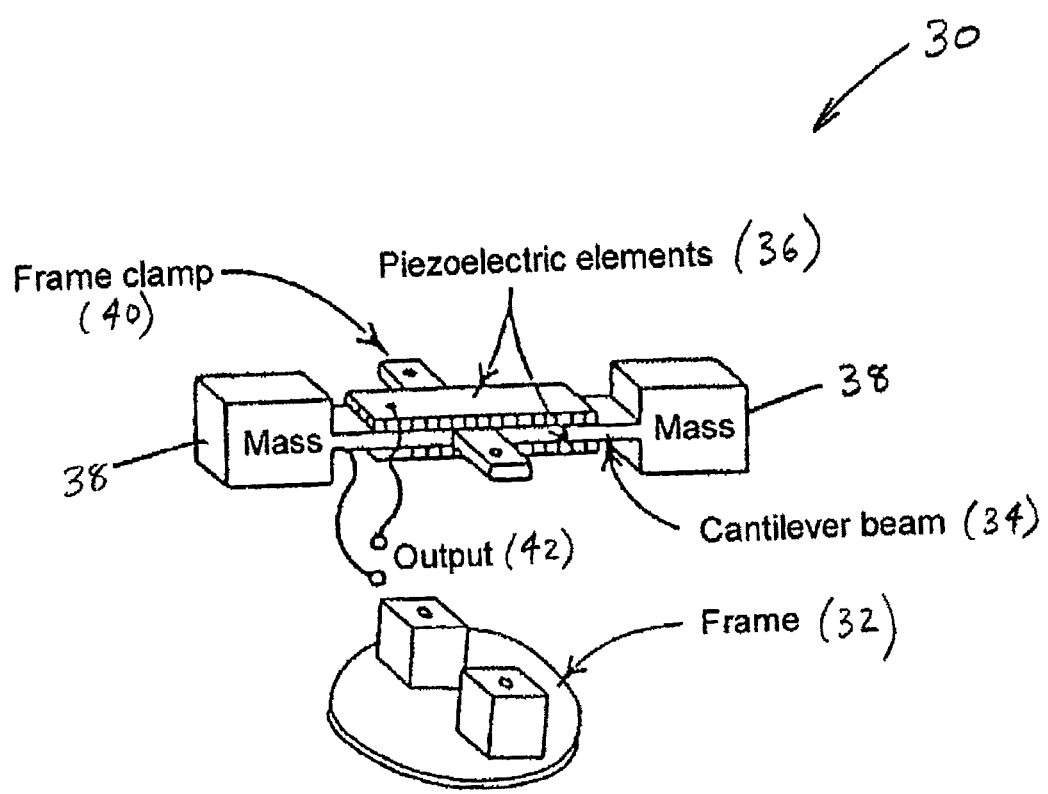
FIG. 2 is diagram showing an accelerometer-type cantilever microphone capable of being used with the present invention.

FIG. 2 is diagram showing an accelerometer-type cantilever microphone 30 capable of being used with systems of the present invention. The microphone 30 includes a frame 32 which is positionable against a patient's chest, a cantilever beam 34 mounted to the frame 32 via frame clamp 40, piezoelectric elements 36 mounted to the cantilever beam 34, and masses 38 mounted to opposite ends of the cantilever beam 34. The operation of the microphone 30 is similar to an accelerometer in that the masses 38 provide an inertial reference, which can be utilized to detect acoustic signals. Chest vibrations (including vibrations caused by the patient's heartbeat) cause the cantilever beam 34 to deflect with respect to the masses 38. This deflection causes an electrical charge to be generated by the piezoelectric elements 36, which generates an electrical signal via output leads 42 corresponding to the vibrations. It has been found that the microphone 30 exhibits good sensitivity up to frequencies of about 2 kHz.

Figure 3:
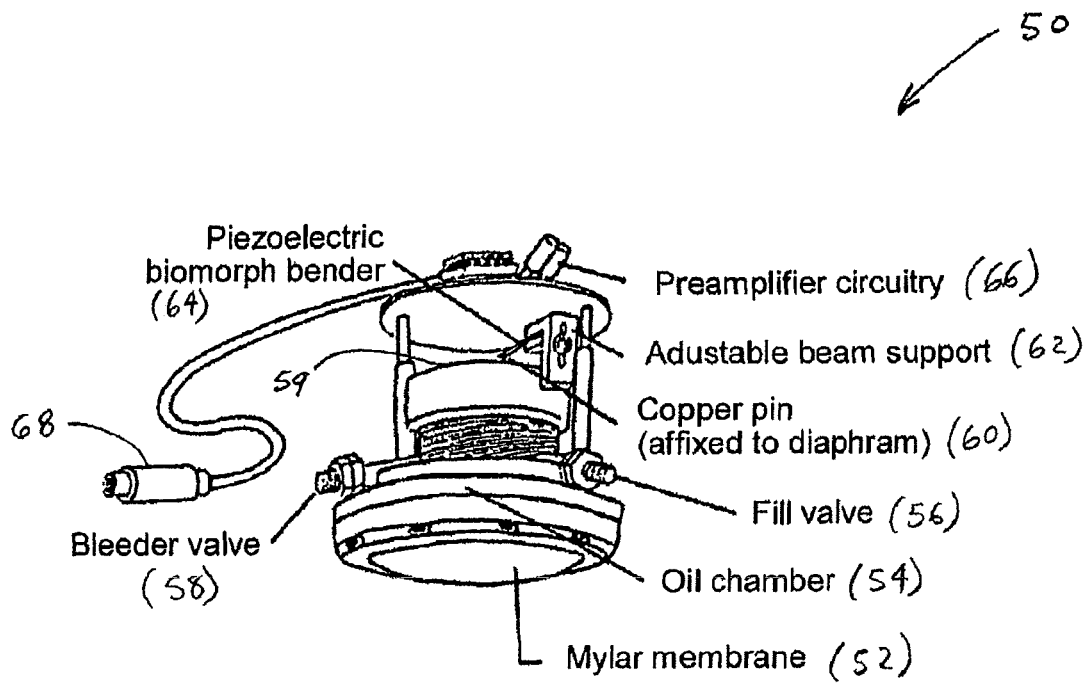
FIG. 3 is a diagram showing an oil-coupled microphone capable of being used with the present invention.

FIG. 3 is a diagram showing an oil-coupled microphone 50 capable of being used with systems of the present invention. The microphone 50 is impedance matched, such that the acoustic impedance of a patient's tissue is matched to that of the microphone 50 via oil stored in an oil chamber 54 and a mylar membrane 52 which contacts the patient's skin. The oil chamber 54 can be filled with oil using a fill valve 56 in fluid communication with the oil chamber 54, and excess oil can be removed from the chamber 54 using a bleeder valve 58, also in fluid communication with the chamber 54. The oil chamber 54 is in communication with a diaphragm 59, such that acoustic vibrations generated by the patient's heart are transmitted from the mylar membrane 52, through the oil chamber 54, and to the diaphragm 59. A copper pin 60 interconnects the diaphragm 59 to a piezoelectric biomorph bender 64 mounted on an adjustable beam support 62. The bender 64 converts the acoustic vibrations to electrical signals which are amplified and/or processed by preamplifier circuitry 66 for transmission via electrical connector 68.

Figure 4:
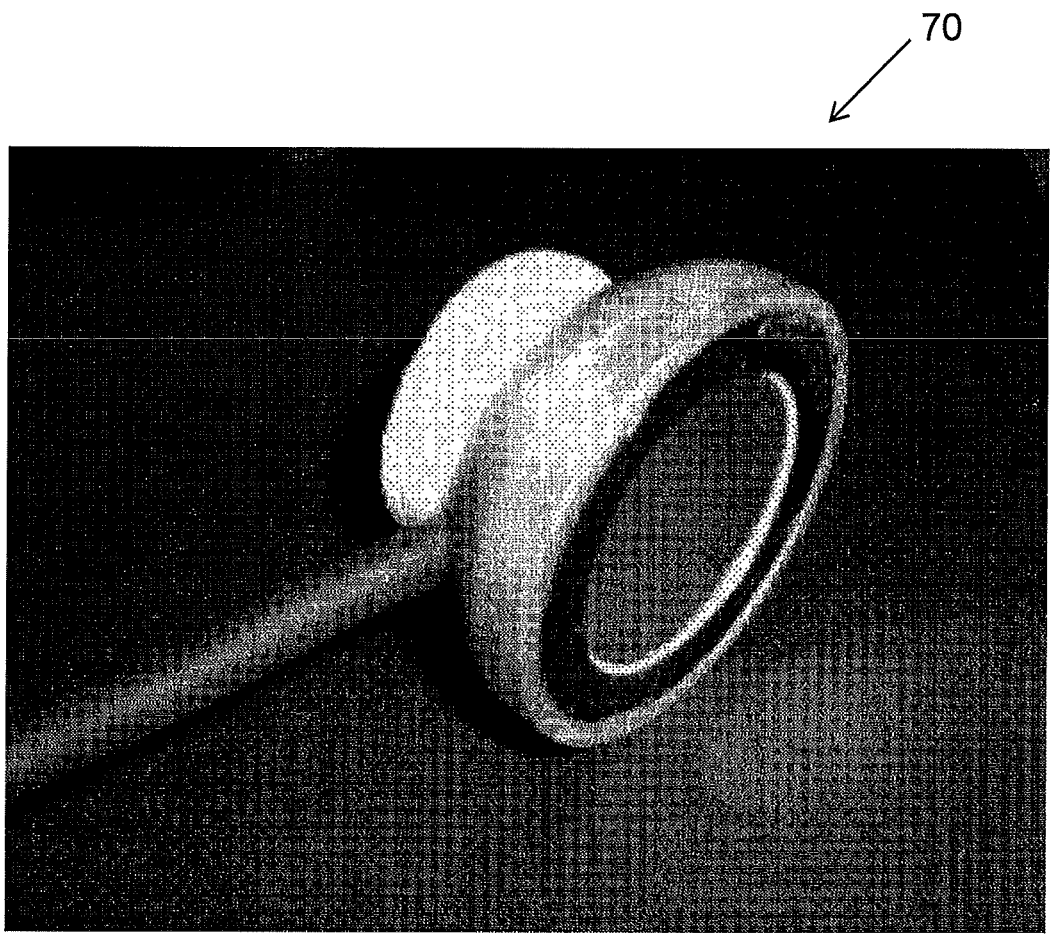
FIG. 4 is a photo of an impedance-matched, gel foam microphone capable of being used with the present invention.

FIG. 4 is a photo of an impedance-matched, get foam microphone 70 capable of being used with systems of the present invention. The microphone 70, manufactured by SonoMedica, Inc. (Sterling, Va.) includes an internal piezoelectric sensor which is acoustically impedance matched with a patient's skin via a coupling gel and foam pad (not shown). The housing of the microphone 70 is designed to be responsive to the compression and rarefaction components of an acoustic heart signal, while rejecting the shear component of the signal, thus providing directionality. The microphone 70 is based on a partial acoustic impedance matching technique, in which a closed volume of air matches impedance between the chest and an air-coupled capacitor microphone. A contact membrane encloses the air chamber to provide some impedance matching between the microphone and the tissue.

It is noted that microphone types and designs other than those discussed above in connection with FIGS. 2-4 could be utilized with the systems of the present invention. Examples of such microphones include, but are not limited to: minimal load, contact-type microphones employing small, lightweight magnets; capacitor microphones having one plate in contact with the patient's skin and a second, rigid plate attached to a frame; transducers having a fluid or a gel in a bladder or pad and a hydrophone or piezoelectric detector; transducers based on piezoelectric detection of photoacoustic signals; impedance-matched microphones having water-based gels; and phased-array detectors which include horizontal and vertical rows of contact microphones.

Figure 5:
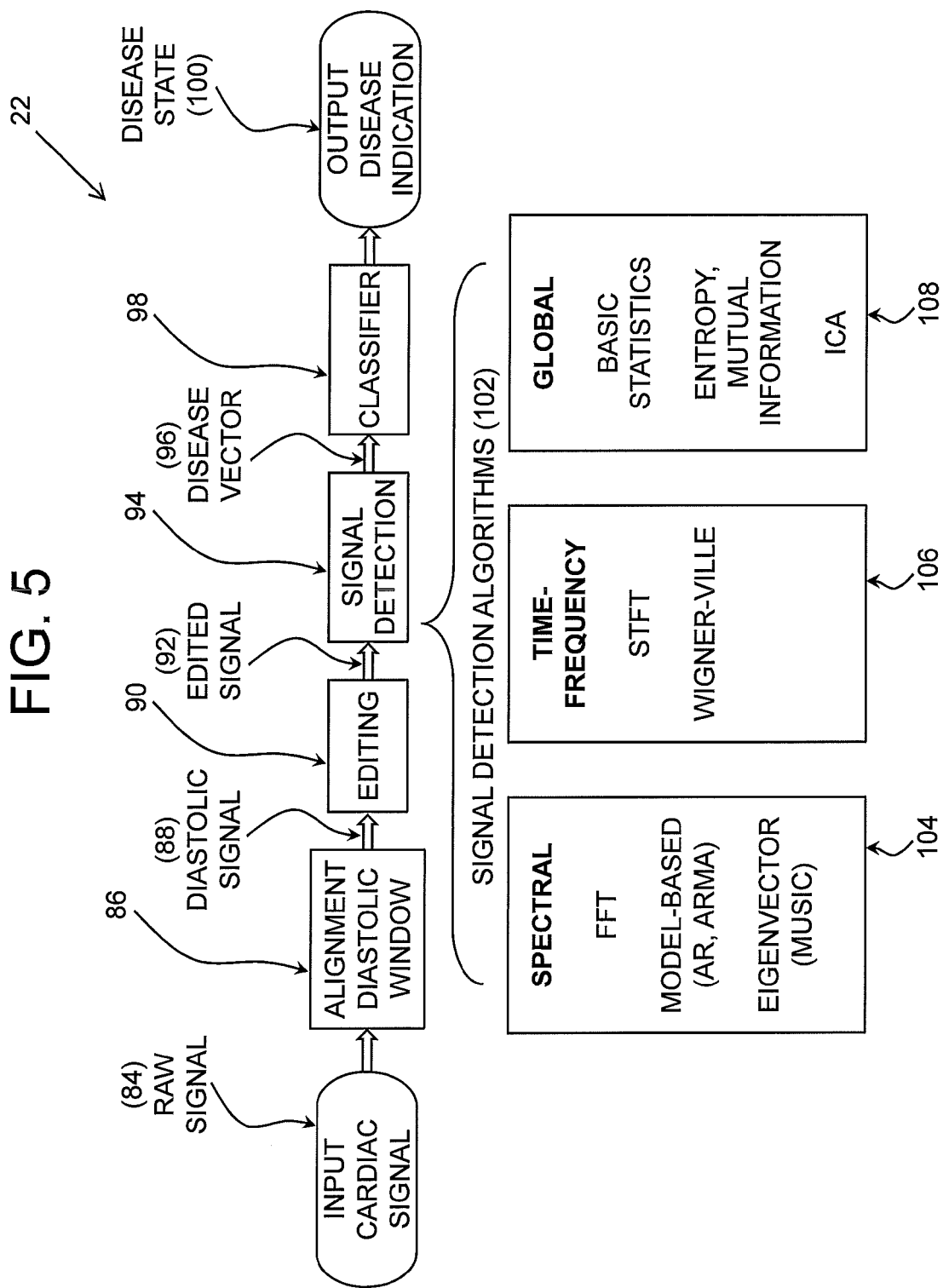
FIG. 5 is a flowchart showing processing steps of the coronary artery disease detection software of the present invention.

FIG. 5 is a flowchart showing an embodiment of the CAD detection software 22 of a system of the present invention in detail. In this embodiment, a raw input cardiac signal 84 (such as the acoustic heart signal detected by the microphone 16 and amplified by the amplifier 18 of FIG. 1) is processed in step 86 to define a diastolic "window" or segment of the detected heart signal which represents isolated portions of the signal which do not contain signals corresponding to heart valve movements. This window corresponds to a relatively quiet segment occurring after sounds generated by the closing of the heart valves. It is during this quiet period that coronary blood flow is maximal, so that the acoustic signature associated with turbulent blood flow is likely to be loudest. The ECG signal monitored by the QRS detector 28 of FIG. 1 can be used as a timing reference to assist with identifying the diastolic segment. The diastolic window, once defined, can be aligned as necessary. The processing of step 86 produces a diastolic signal 88 which is processed by editing step 90.

In step 90, the isolated diastolic signal 88 is automatically edited to remove noise or any undesired artifacts in the signal, to produce an edited signal 92. The editing step 90 also allows a user to save information about previously-rejected records, including the number and reason why a diastolic segment was eliminated from a patient data set.

In step 94, the edited signal 92 is processed by a plurality of signal detection algorithms 102, which include spectral analysis algorithms 104, time-frequency detection algorithms 106, and global detection algorithms 108, to generate a disease vector 96 containing the following feature parameters which are useful in detecting CAD:

TABLE 1

| Feature Parameter Number | Feature Parameter Name | Feature Description |
|---|---|---|
| 1 | Nu eliminated | Number of segments having noise |
| 2 | Nu edited | Number of segments accepted |
| 3 | Nu count | No. of points in a segment having amplitude greater than a constant ('outlier') times the standard deviation of complete cycle |
| 4 | Nu peak | Mean of ratio of maximum amplitude of each segment to maximum amplitude in the record |
| 5 | Nu shape | Mean of ratio of sum of the AR spectrum of each segment to the sum of the AR averaged spectrum for the entire record |
| 6 | Total count | Number of segment not deleted |
| 7 | Std peak | Standard deviation of ratio of maximum amplitude of each segment to maximum amplitude in the record |
| 8 | Std shape | Standard deviation of ratio of sum of the AR spectrum of each segment to the sum of the AR averaged spectrum for the entire record |
| 9 | Var peak | Variance of ratio of maximum amplitude of each segment to maximum amplitude in the record |
| 10 | Var shape | Variance of the ratio of the sum of the AR spectrum of each segment to the sum of AR averaged spectrum for the entire record |
| 11 | Max peak | Highest amplitude of data in ratio of maximum amplitude of each segment to maximum amplitude in the entire record |
| 12 | Kurtosis | Mean of Kurtosis of each segment |
| 13 | Pmusic | Mean of the ratio of high-to-low frequency energy obtained with the MUSIC method (subspace = 27) |
| 14 | Pmusic var | Variance of the above parameter (subspace = 27) |
| 15 | Information | Mutual Information segment by segment comparison of the mutual information between each segment in the record |
| 16 | Information std | Standard deviation of the above parameter |
| 17 | information_fft | Mutual information segment by segment comparison of the mutual of the spectrum of each segment is compared. The Fourier transform was used to calculate the spectrum |
| 18 | information_avg | The mutual information between each segment and the average of the entire record |
| 19 | info. Avg_std | Standard deviation of the above parameter |
| 20 | Negentropy | Mean of negentropy of each segment in a record |
| 21 | Negentropy_std | Standard deviation of the above parameter |
| 22 | Negentropy_kurt | Kurtosis of the Negentropy parameter |
| 23 | Eigen ratio 1/2 | Ratio of $1^{st}$ and $2^{nd}$ eigenvalues obtained by PCA |
| 24 | Eigen1 | Value of $1^{st}$ eigenvalue obtained by PCA |
| 25 | Value Max. Hist | Time-frequency analysis (See text) |
| 26 | FFT | Mean of Fourier transform of each segment |
| 27 | Power FFT | Mean of Power spectral density of each record |
| 28 | Ar hi/lo peaks | Subtraction of maximum value of average of AR spectrum found in the low frequency and high frequency range. (AR order = 9) |
| 29 | pwelch_power | Sum of ratio of average Power spectral density in the high frequency region to the average Power spectral density in low frequency region of each segment. (MATLAB default values) |
| 30 | pwelch_var | Variance in the Power spectral density in the high frequency region to the variance in the Power spectral density in low frequency region. (MATLAB default values) |
| 31 | Pwelch | Mean of Power spectral density of each segment. (MATLAB default values) |
| 32 | mutual delay | Mutual information of each segment compared with the next 10 segment in the record |
| 33 | std delay | Standard deviation of the above parameter |

The spectral analysis algorithms 104 allow for assessment of heart sound frequency spectra, and include, but are not limited to: fast Fourier transform (FFT); parametric, autoregressive (AR) methods; and Eigenvector analysis methods such as Multiple Signal classification methods (referred to as "MUSIC" methods). These algorithms can be used to generate feature parameters associated with frequency spectrum characteristics of the edited heart signal, which can be used to classify whether a heart signal is indicative of CAD. In particular, the spectral algorithms 104 can be used to analyze for the presence of narrow-band frequencies or resonances in the edited signal which are indicative of the presence of CAD. Such frequencies or resonances are produced by turbulent blood flows which result from the presence of CAD in an artery, and are thus indicative of the presence of CAD. It has been found that the MUSIC spectral analysis algorithm is particularly effective at eliminating spectral peaks and narrowband processes at high noise levels.

The time-frequency algorithms 106 allow for analysis of resonances over specific frequencies and times. These algorithms include, but are not limited to, short-term Fourier Transform (STFT), Wigner-Ville distribution, continuous wavelet transform, and the "FMS" detection algorithm developed by SonoMedica, Inc., which is based on parameters extracted from the STFT algorithm.

The global detection algorithms 108 allow for the capturing and analysis of data set characteristics relating to inter-segment variability, segment non-Gaussianity, and general structure features of the edited signal. Variability parameters are based on the segment-to-segment variance of other feature parameters. Measures of non-Gaussianity include kurtosis and other higher-order moments, and are useful since signals associated with turbulence are generally non-Gaussian. Feature parameters associated with general structure include a measurement of negative entropy, a measurement of mutual information, and parameters related to independent component analysis.

After processing of the edited signal 92 in step 94 using the signal detection algorithms 102 to produce the disease vector 96, the disease vector 96 is then classified in step 98 to determine the presence or absence of CAD in a patient, indicated by an output disease state indication 100. The disease vector 96 is preferably processed by a support vector machine (SVM) to determine if the pattern of parameters contained in the vector 96 is characteristic of a normal or a diseased patient. SVMs provide a pattern recognition operation by grouping disease vector patterns into normal and diseased groups, and produce optimal boundaries to separate classes. If the input pattern is not linearly separable, SVMs can automatically transform the data into a higher-dimensional space to effectively construct non-linear boundaries between the classes. If the dimension is high enough, linear separation is guaranteed. Unlike discriminant analysis, where all of the data is considered, support vectors are boundaries established by the data points in each class that are closest to the other class. As a result, support vectors are concerned with the problematic data points where separation between classes is minimal, and provide optimal separation between the closest points. Other classifiers can separate training data with a high degree of accuracy, but a major advantage of the SVM classifier is that it not only performs well on training data, but it also performs well on test set data. It is noted that other classification techniques, such as linear discriminant analysis or adaptive neural network (ANN) analysis, could also be utilized.

Recordings from one or more of the transducer sites described below in connection with FIG. 7 can be analyzed under a number of different conditions, including: gender separated or combined; sites separated or combined; and edited or unedited. For each of these conditions, each feature parameter listed above in connection with Table 1 can be analyzed using the aforementioned SVM classifier.

Figure 6:
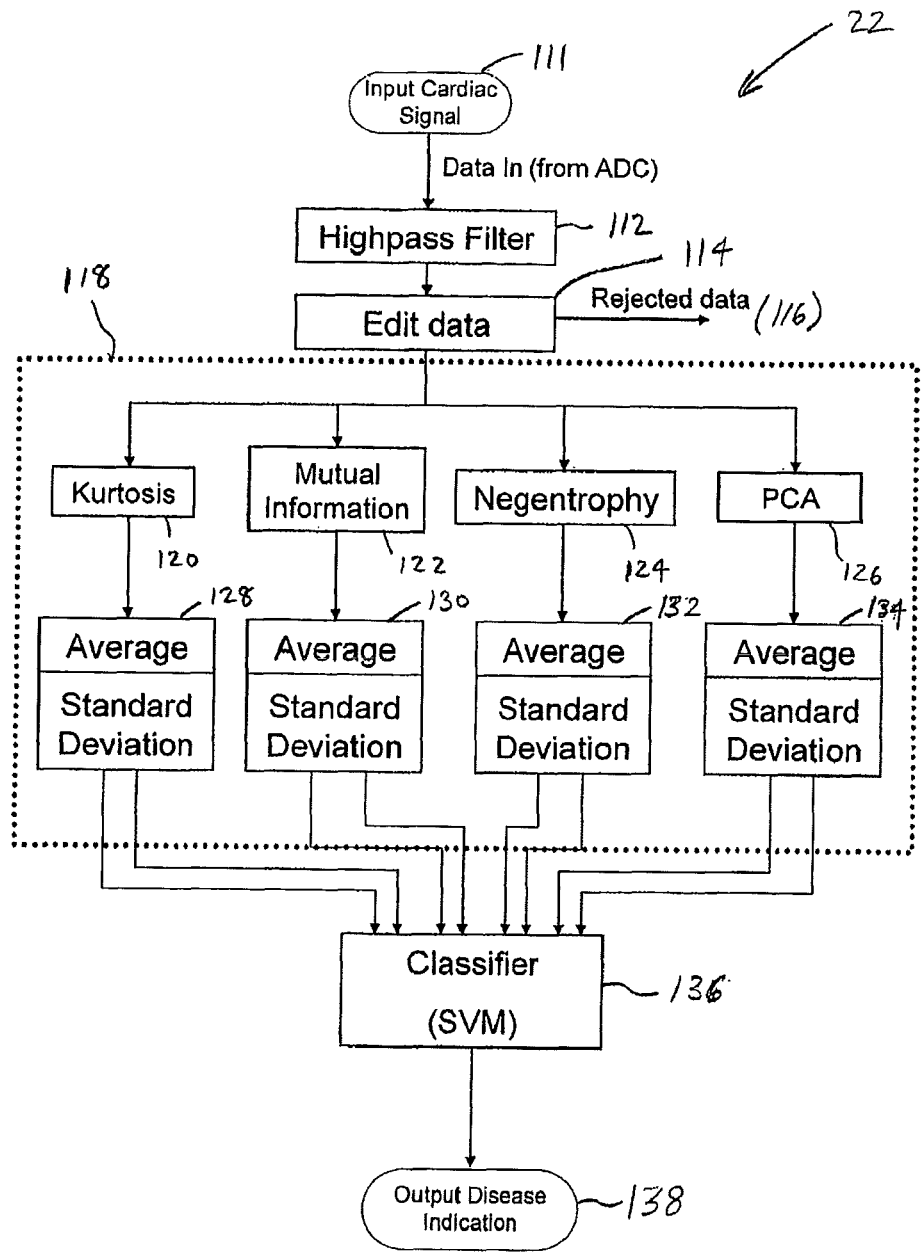
FIG. 6 is a flowchart showing the coronary artery disease detection software of the present invention in greater detail.

FIG. 6 is a flowchart showing this embodiment of the CAD detection software 22 of a system of the present invention in greater detail. As mentioned above, the input cardiac signals are processed by a plurality of signal processing algorithms to detect the presence of CAD. As shown in FIG. 6, such signal processing algorithms can include kurtosis, mutual information, negentropy, and principal component analysis (PCA) processing algorithms.

In step 112, the input cardiac signal 111 (which has been digitized by an analog-to-digital converter (ADC)) is filtered by a high-pass digital filter (preferably, an 8-pole Butterworth filter, but other filters can be used) having a cutoff frequency of 180 Hz. The filtered data is then edited in step 114 in accordance with the editing step described above in connection with FIG. 5, to remove excessive noise. The editing procedure 114 applies the tests described in Table 2 below on the data, and rejects any data which exceeds threshold criteria of the tests. The rejected data 116 removed as a result of the editing process are discarded.

TABLE 2

| Test Number | Description and Elimination Criteria |
|---|---|
| 1 | Ratio of the sum of the AR output of each cycle to the sum of the AR output of the entire record exceeds the shape threshold ("shape_diff_thresh") |
| 2 | Ratio of maximum amplitude of each cycle to maximum amplitude in the record exceeds peak threshold ("peak_diff_thresh") |
| 3 | Maximum amplitude in each cycle exceeds threshold ("max_peak_thresh") times the average standard deviation of whole record |
| 4 | Number of points in a cycle exceeding threshold ("outlier_thresh") times standard deviation of an overall cycle exceeds a limit ("outlier_limit") |
| 5 | Maximum amplitude in an overall cycle exceeds twice the maximum amplitude of the cycle in the first half of the frequency spectrum |
| 6 | Maximum amplitude of the cycle in the range of 650 Hz to 800 Hz exceeds 8 times the mean of spectral characteristics of the cycle in the first half of the frequency spectrum |

In step 118, data which passes the editing tests are processed by detection algorithms 120-126, which include, but are not limited to, kurtosis 120, mutual information 122, negentropy 124, and PCA 126. The algorithms 120-126 quantify the non-Gaussian characteristics of the data. These and other tests produce the variable listed above in Table 1.

The kurtosis algorithm 120 represents the simplest statistical quantity processing algorithm for indicating the non-Gaussianity of a random variable. Kurtosis is related to the fourth-order moment (and the fourth-order cumulent), and for zero-mean data, is expressed as:

$$\mathrm{kurt}(x) = E\{x^4\} - 3[E\{x^2\}]^2 \quad (1)$$

where E indicates the expectation of the related argument. Kurtosis has the advantage of being very easy to calculate, but since it contains values of the data raised to the fourth power, it is strongly influenced by outliers and is not very robust to noise. For the same reason, kurtosis is also less influenced by the central range of the data which is likely to be where most of the structure lies. For zero mean data the fourth-order cumulent is the same as kurtosis. Cumulents carry the same statistical information as their respective moments, but have some additional desirable properties.

The mutual information (MI) processing algorithm 122 is related to both non-Gaussianity and negentropy, and can be used as a measure of structure. The concept of mutual information is well-developed and also provides a link between negentropy and maximum likelihood. Mutual information can be expressed mathematically as:

$$I(x^1, x^2, \ldots x^n) = \Sigma^n_{i=1} H(x_i) - H(x) \quad (2)$$

where I is the mutual information between n random variables, and x is a vector containing all the variables $x_i$. The measurement of MI could be applied to data within a single cycle, but is preferably used to determine mutual information between cardiac cycles (each $x_i$ representing a different cardiac cycle). The presence of structure increases the mutual information between different cycles as long as the structural characteristics are present in multiple cycles. This can provide a very sensitive test for structure across a number of cardiac cycles.

MI can be used as the basis for quantifying independence in many independent component analysis (ICA) algorithms, and has a number of applications in medical signal processing including image analysis (feature extraction), image registration, and EEG analysis. These applications have motivated the development of several different approaches for estimating the MI of a data stream. Some of the algorithms for determining negentropy can also be used to determine MI. The most common method for estimating MI partitions the data into bins to approximate the marginal densities of the two variables of interest. Other approaches are based on petitioning into hierarchical nested hyper-rectangles, the entropy estimates of k-nearest neighbor distances, kernel density estimators, empirical classification, and local expansion of entropy.

The negentropy processing algorithm 124 provides noise immunity while allowing for detection of CAD. Negentropy is a differential entropy, and specifically, represents the entropy of the variable of interest subtracted from the entropy of a Gaussian variable having the same variance. Negentropy can be described as:

$$J(x) = H(x_{gauss}) - H(x) \quad (3)$$

where the entropy, $H$, is defined as:

$$H(x) = \sum_i p(x = \alpha_i) \log p(x = \alpha_i)$$

The classic method of approximating negentropy is based on the polynomial density expansion and uses the higher-order cumulants of kurtosis (fourth-order) and skewness (third-order), expressed mathematically as follows:

$$J(x) \approx \tfrac{1}{12} \text{skew}(x)^2 + \tfrac{1}{48} \text{kurt}(x)^2 \quad (4)$$

where the skewness, skew(x), is defined as: skew(x)=$E\{x^3\}$).

A more robust method for approximating negentropy uses nonlinear functions to reduce the range of the data and reduce the influence of outliers and data at the extremes, expressed as follows:

$$J(x) \approx k_1 (E\{G_1(x)\})^2 + k_2 (E\{G_2(x)\} - E\{G_2(\upsilon)\}) \quad (5)$$

where $G_1(x)$ and $G_2(x)$ are, in principle, any two non-quadratic functions and $\upsilon$ is a Gaussian variable of zero mean and unit variance. This equation assumes data with zero mean. The two functions are designed to capture the information provided by the third- and fourth-order cumulents in Equation 4 above, but be less sensitive to outliers. Additionally, $G_1(x)$ can be made an odd function and $G_2(x)$ and even function. Choosing functions that do not grow too fast with increasing values of x also leads to more robust estimators. Two functions that have been shown to work well in practice are:

$$G_1(x) = 1/\alpha \log(\cos h(\alpha x)) \quad (6)$$

$$G_2(x) = -e^{(-y^2/2)} \quad (7)$$

The principal component analysis (PCA) algorithm 126 uses a standard singular value decomposition to find the principal components. Singular value decomposition decomposes the data matrix, X, into a diagonal matrix, D, containing the square root of the eigenvalues and a principal components matrix, U:

$$X = U^* D 1/2 U' \quad (8)$$

Only the first two eigenvalues of the principal components are used for detection.

Each of these algorithms 120-124 generates a single parameter for each cycle of data, and the PCA algorithm 126 generates two parameters. These parameters are passed to average and standard deviation operations 128-134, each of which determines the mean and standard deviation for these parameters over all cycles. These parameters, when grouped together from the disease vector, are then passed to the classifier algorithm 136 to determine the disease state and to produce an output disease indication 138.

The classifier algorithm 136 could use any of a variety of known classification schemes, and preferably, a Support Vector Machine (SVM), discussed above. One advantage of this type of classifier is that it is very general in nature and can find optimal classification boundaries for complex and non-linear data sets.

It is noted that the processing steps of this embodiment of the present invention described herein can be embodied as computer software, and associated software modules, which are executed by any suitable computer system, such as the computer hardware discussed above in connection with FIG. 1. Such modules could be written in any suitable high- or low-level programming language (such as C, C++, MATLAB, Java, Visual Basic etc.) which can be executed as object code by a computer system.

Figure 7:
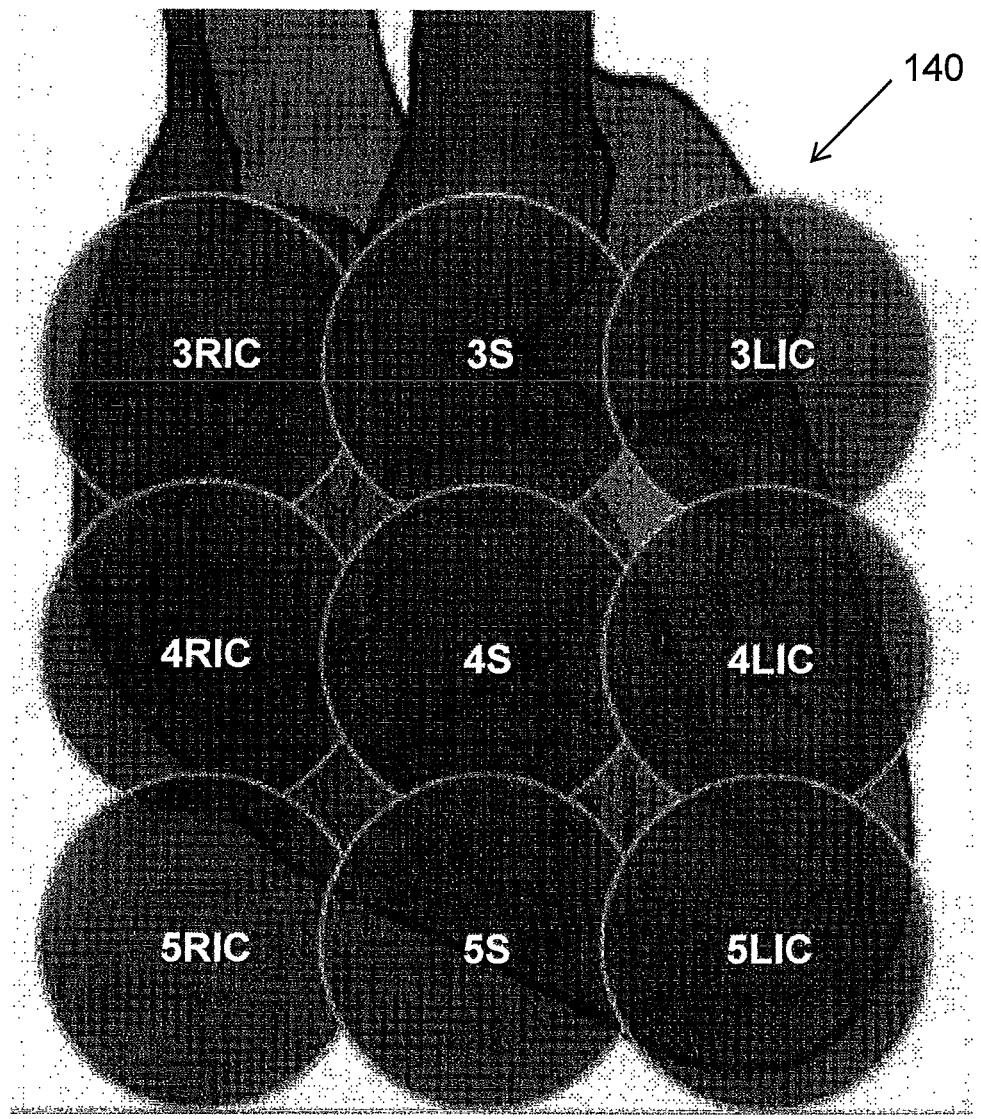
FIG. 7 is a diagram showing locations for positioning the microphone of the present invention for acoustically detecting coronary artery disease.

FIG. 7 is a diagram, indicated generally at 140, showing locations for positioning the microphone of the present invention for acoustically detecting coronary artery disease. One suitable technique for taking acoustic measurements of heart signals is the protocol developed by SonoMedica, Inc., wherein measurements are taken at the third, fourth, and fifth intercostals spaces and along the sternum. In the SonoMedica protocol, patient heart sounds and ECG are recorded when the patient is sitting up in a comfortable, high-back chair, which brings the heart closer to the chest wall that if the patient is in a prone position. Preferably, the examination room is quiet, but need not be soundproof. Locations for the microphone are chosen so that sounds can be recorded from the major coronary vessels, including the left main vessel, the left anterior descending vessel and its branches, the left circumflex and its branches, and right coronary artery and its branches. Preferably, sounds are recorded at nine locations, including at three right intercostal locations 3RIC, 4RIC, and 5RIC in FIG. 7, at three sternum locations 3S, 4S, and 5S in FIG. 7, and a three left intercostal locations 3LIC, 4LIC, and 5LIC in FIG. 7. Other, or any other number, of locations could be utilized without departing from the spirit or scope of the present invention. Preferably, 30 seconds of acoustic data are recorded at each location shown in FIG. 7.

Figure 8:
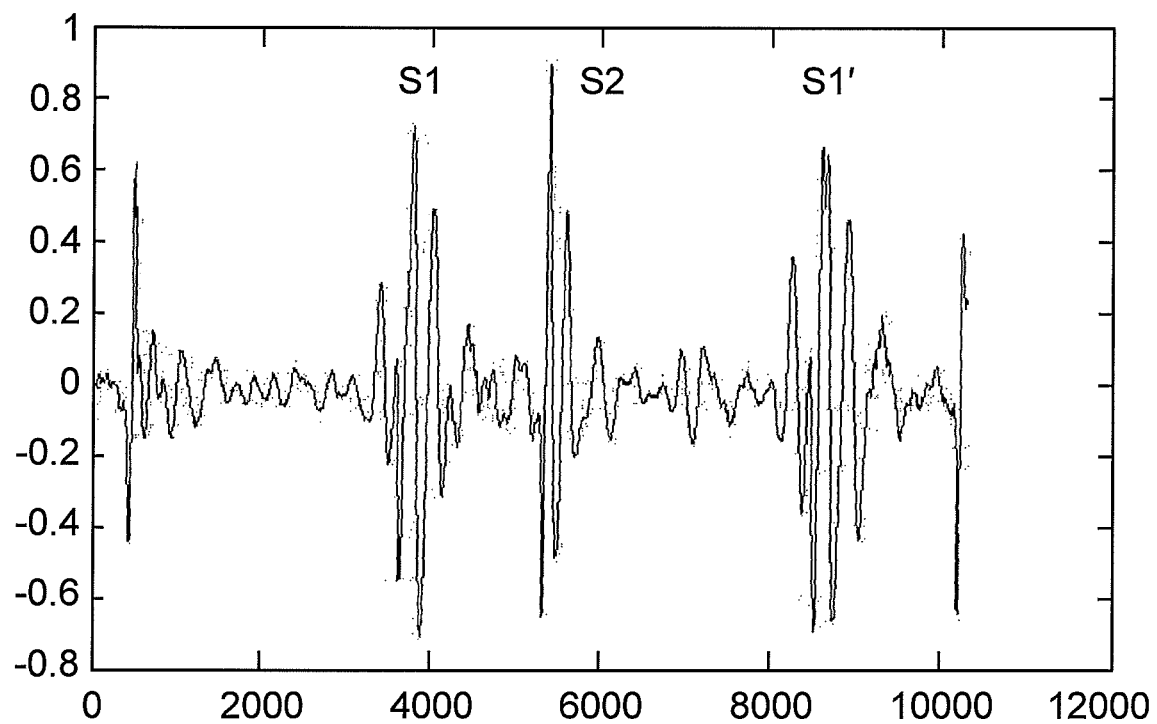
FIG. 8 is a phonocardiograph showing acoustic heart signals detected by the present invention.

FIG. 8 is a phonocardiograph showing acoustic heart signals detected by a system of the present invention. Typically, a human heart beat generates two distinct sound patterns corresponding to movement of the heart valves, i.e., first and second heart valve sounds. These sounds are labeled in FIG. 8 as first and second heart valve sounds S1 and S2, respectively. The first heart valve sound of the next heartbeat is labeled as S1'. The portion of the heart signal most useful for detecting CAD occurs after the second heart valve sound S2, i.e., between the heart valve sounds S2 and S1' in FIG. 8. As will be discussed below, the present invention allows for the flexible definition of a diastolic "window" between the heart valve sounds S2 and S1' so as to optimize the detection of CAD in a patient.

Figure 9:
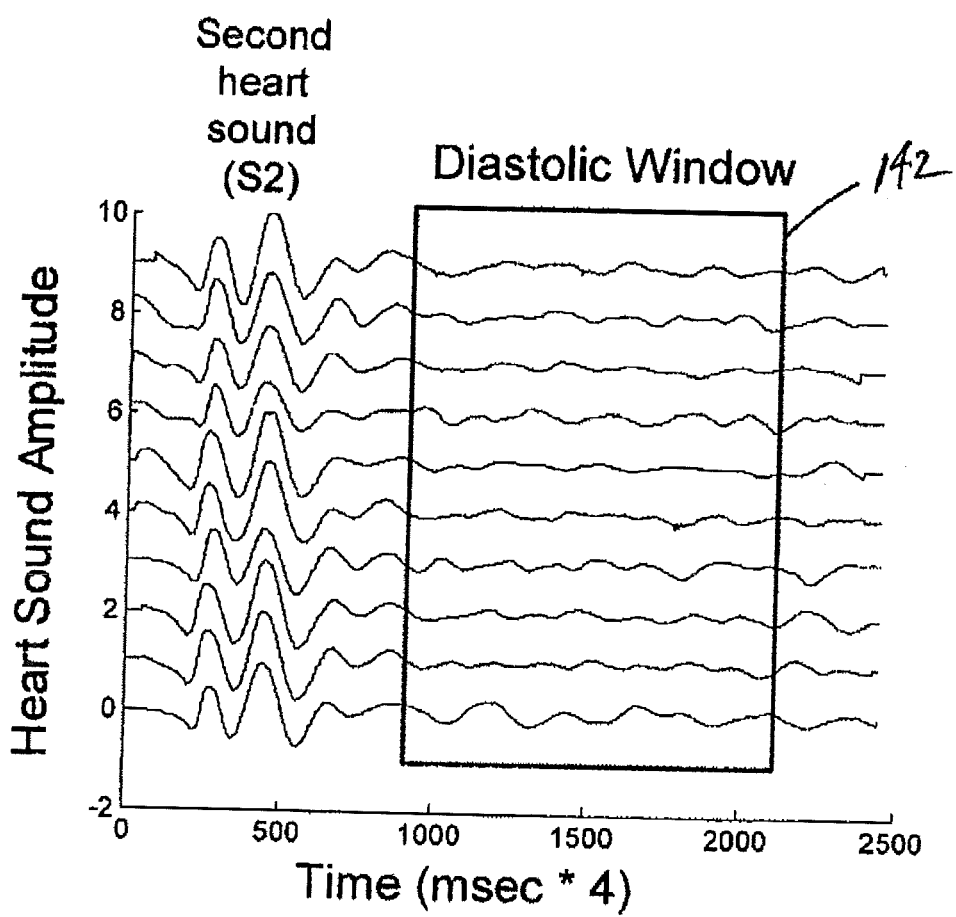
FIG. 9 is a phonocardiograph showing the diastolic window of the present invention for defining a range of heart signals for analysis.

FIG. 9 is a phonocardiograph showing the diastolic window of a system of the present invention, indicated generally at 142, for defining a range of heart signals for analysis. The diastolic window 142 is preferably defined after the second heart valve sound S2, so as to optimize the detection of CAD. The diastolic window 142 includes signals which correspond to the diastolic segment of a heartbeat, and have been found to be of value in detecting CAD because valve sounds are absent from the signal in the diastolic window 142 and coronary blood flow is maximal, thus providing quality signals for analysis. As a result, acoustic signatures associated with turbulence are best detected during this period. Optionally, the diastolic window 142 can be more accurately defined by applying cross-correlation techniques to the second heart valve sound S2. It is noted that an automated procedure for the defining the diastolic window 142 can be utilized, such as the automated diastolic window definition procedure developed by SonoMedica, Inc. In FIG. 9, ten heart samples are shown, but any number of heart samples could be utilized.

Figure 10:
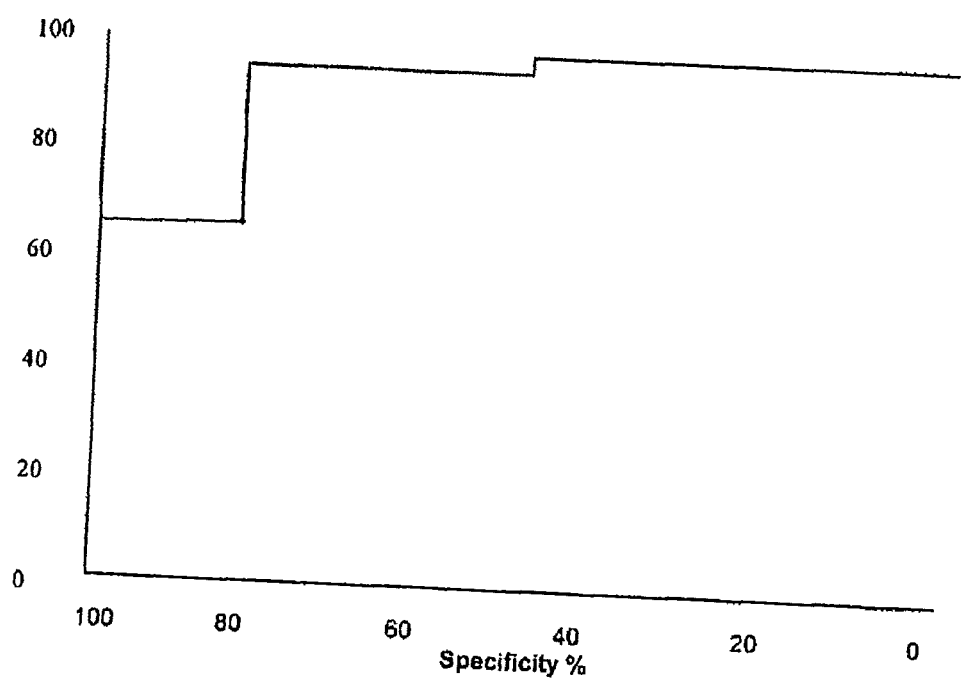
FIGS. 10-11 are graphs comparing the sensitivities and specificities of detected heart signals.
Figure 11:
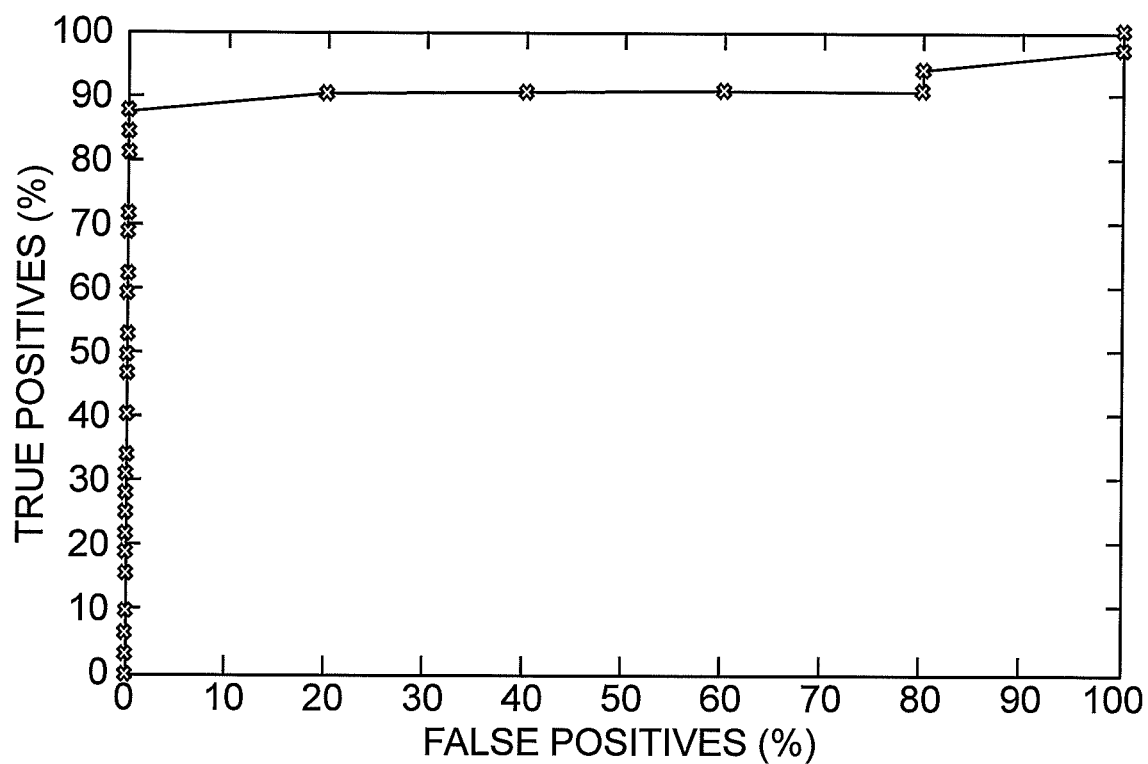

FIGS. 10-11 are graphs comparing the sensitivities and specificities of detected heart signals. Graphed in FIG. 10 is the standard deviation of the maximum amplitude in each sampled heart segment, normalized by the maximum amplitude in the record. This graphed feature corresponds to feature parameter number 8 in Table 1 above. This feature parameter has been shown to yield the most accurate sensitivity/specificity curve if only a single feature is used out of the feature parameters discussed above. FIG. 11 shows the sensitivity/specificity curve generated by the present invention for another single feature: the maximum amplitude of each sampled heart segment normalized by the maximum amplitude in the record. As can be seen, this feature parameter allows for the correct detection of approximately 87% of individuals having CAD, with no misclassification of individuals of normal health. When combined with processing using one or more of the signal detection algorithms disclosed herein, more accurate detection of CAD can be achieved.

Figure 12:
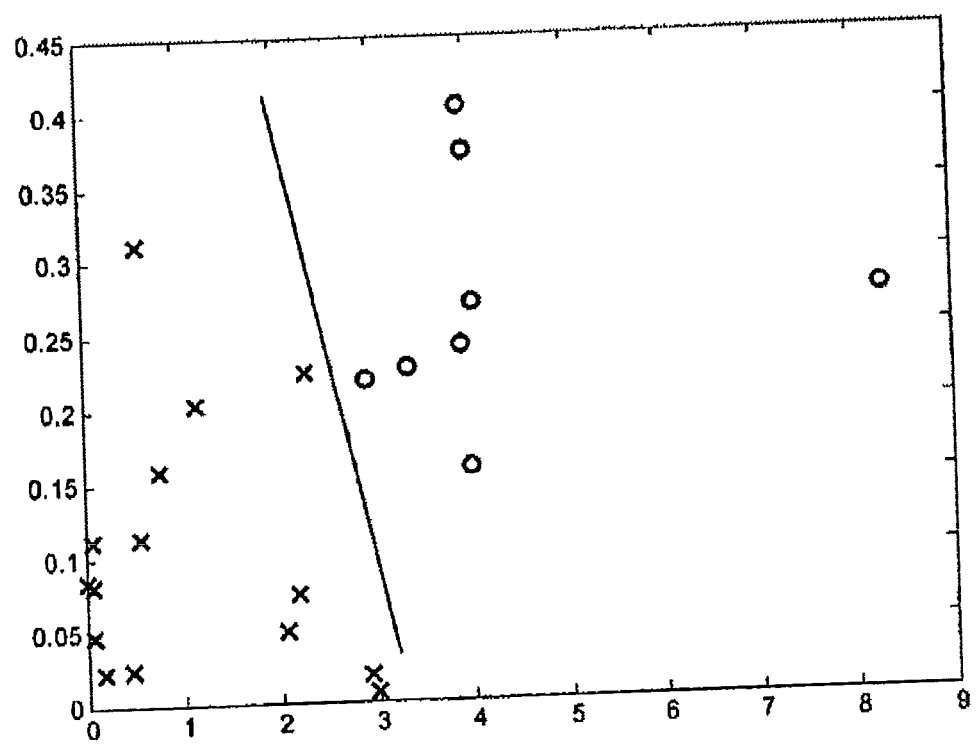
FIG. 12 is a graph showing discriminant analysis applied by the present invention to both normal and diseased patients for determining the presence of coronary artery disease.

FIG. 12 is a graph showing simple linear discriminant analysis applied by a system of the present invention to both normal and diseased patients for determining the presence of coronary artery disease. As mentioned above, one or more feature parameters of the acoustic signal (i.e., a feature parameter acquired through editing of the acoustic signal or processing of the acoustic signal using one or more of the signal processing algorithms of the present invention, as described above) can be utilized to indicate the presence of CAD in a patient when the feature parameter exceeds a pre-determined threshold. The pre-determined threshold can be defined by applying linear discriminant analysis to plots of sample patient data for individuals with CAD and without CAD, as shown in FIG. 12.

As shown in FIG. 12, the values of two feature parameters are plotted against one another. The parameter combinations from diseased patients are plotted as Xs, while the parameter combinations from normal individuals are plotted as Os. Feature parameters 4 and 11 from Table 1, above, were plotted together, and allowed for the generation of a discriminant between the two groups (represented by the solid line in the graph). This simple linear discriminant can thus be used to determine the presence or absence of CAD for patients in this data set. Larger data sets allow for the inclusion of more of the parameters listed in Table 1 in the decision process. When many parameters are involved, the SVM classifier can be used to decide if a parameter pattern is related to that of a normal or a diseased patient.

It is noted that linear discriminant analysis can optimize the placement of a linear boundary, such as the discriminant shown in FIG. 12. Non-linear methods, such as support vector machines (SVM), adaptive neural nets, and flexible discriminants, can also be utilized to establish thresholds for determining the presence or absence of CAD in a patient. Additionally, features relating to chaotic behavior could also be analyzed in acoustic heart signals, which are indicative of turbulent flows in the blood. Still further, it is conceivable that fractal analysis algorithms for analyzing fractal behavior (based on dimensional analysis) could be utilized to provide additional parameters useful for the detection of CAD in a patient.

Figure 13:
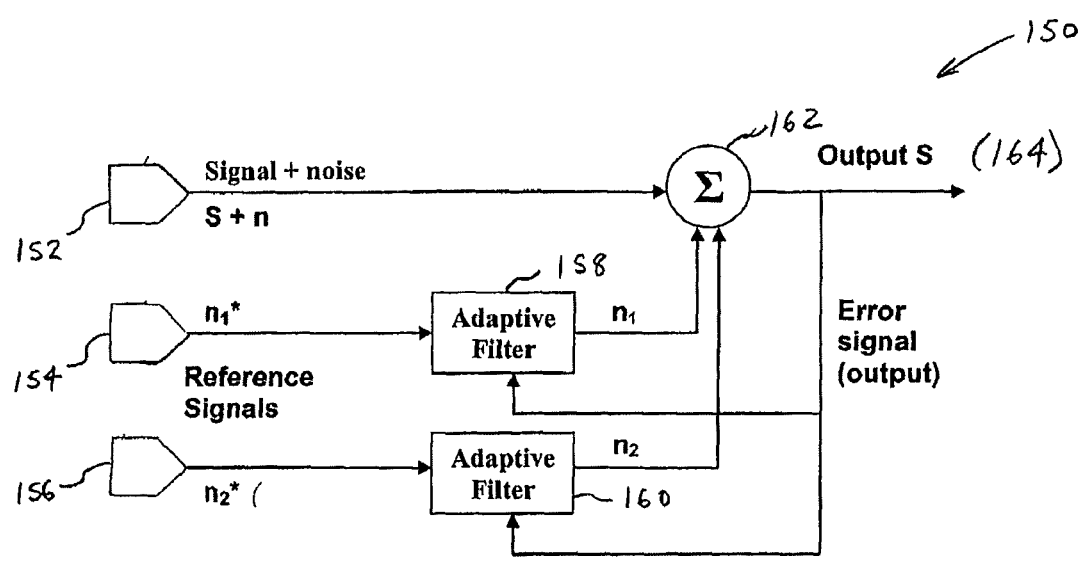
FIG. 13 is a block diagram of an algorithm according to the present invention for reducing noise in detected heart signals.

FIG. 13 is a block diagram of an algorithm to the present invention, indicated generally at 150, for reducing noise in detected heart signals. The circuit 150 applies adaptive noise cancellation (ANC) techniques to remove noise signals from the sampled acoustic heart signal. In one embodiment, three transducers (e.g., microphones, etc.) 152-156 are utilized, wherein the first transducer 152 is placed close to the heart, and the transducers 154-156 are placed away from the heart, and serve as reference transducers. A single reference transducer, or more than two, could also be used. The transducer 152 produces a heart signal S as well as noise n. The reference transducers 154-156 provide reference noise signals $n_1^*$ and $n_2^*$, which are fed to adaptive filters 158 and 160. The filters 158 and 160 are adjusted so that they produce noise signals $n_1$ and $n_2$, which closely match the noise signal n obtained by the microphone 152. The signals $n_1$ and $n_2$ are fed to a subtraction process 162, such that the noise signal n is removed, leaving the output signal S (indicated by reference numeral 164). Any remaining noise components of the output signal S are fed back to the adaptive filters 158 and 160, so that the remaining noise is removed from the signal via an adaptive technique. The root-mean squared (RMS) value, or any other measure of signal energy, can be used to adjust the filters 158 and 160. Since the filters 158 and 160 contain no information about the signal S, they function only to reduce the noise component in the signal, thus having no adverse effect on the signal S.

During use, the transducer 152 can be placed near (e.g., above) the heart, the reference transducer 154 can be placed on the stomach, and the remaining reference transducer 156 can be placed on the left shoulder. This allows for the detection of both internal and external noise. A least-mean square algorithm could be utilized to adjust the filter weights of the filters 158 and 160 adaptively, so as to achieve maximum noise cancellation, wherein the number of weights used in the filters, as well as the convergence gains, can be adjusted as desired. The effectiveness of the two reference microphones 154 and 156 can be estimated by examining the values of the respective filter weights, such that large weights imply an effective channel, while small weights indicate that the channel is of marginal value and zero weights indicate that the reference channel is of no use with respect to noise cancellation.

The noise signals can be processed by a computer to compute a first artifact score, and the weights from the adaptive filters 158 and 160 can be processed utilizing signals from the reference transducers to obtain a second artifact score. The first and second artifact scores can be combined to obtain an overall artifact score which indicates the quality of the data in the transducer 152. These scores can be evaluated for different placement of the reference microphones 154 and 156 so as to determine the placement which provides the highest data quality and which to maximizes adaptive cancellation of noise from heart sounds picked up by the transducer 152.

Figure 14:
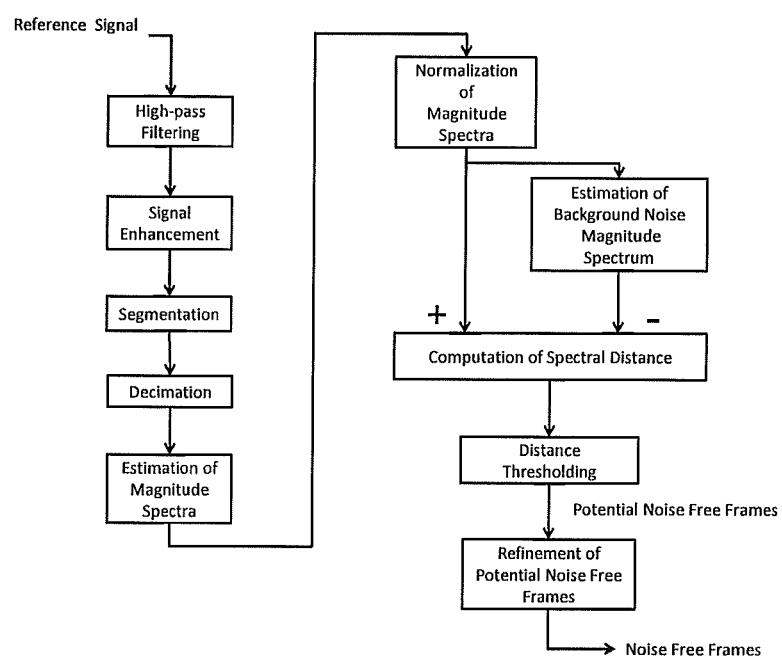
FIG. 14 is a block diagram of steps involved in clinical noise detection.

In another embodiment, in addition to the transducer or active microphone near the heart, a reference microphone is placed on the right abdomen to capture external noise from, for example, talking, nearby machines, intercom and furniture movements, as well as internal noise primarily from stomach rumbles. "Clinical noise" as used herein refers to both external and internal noise. Placement of the reference microphone on the right abdomen ensures capture of clinical noise but avoids interference from the heart sounds. In step 1 of this embodiment of the present invention, the signal from the reference microphone is processed to identify potential noisy segments. In step 2 of this embodiment of the present invention, evaluation is then made to determine the influence of the identified noisy segments on the signals recorded by the active microphone. Only noise segments that have identifiable components in the active channel data are removed. This evaluation step is useful since low level stomach rumbles, for example, do not always corrupt the heart sound recording and therefore need not always be removed. In step 3 of this embodiment of the present invention, data from the active channel is edited to remove the noisy segments. FIG. 14 is a block diagram showing a nonlimiting embodiment of steps involved in clinical noise detection in accordance with the present invention.

In one nonlimiting embodiment, potential noisy segments are identified using 4 subcomponents. The subcomponents of this nonlimiting embodiment comprise a high pass filter signal, signal enhancement, calculation of short-term log variance and identification of noisy segments.

It has been shown previously that the CAD murmurs are above 100 Hz. Therefore, the first subcomponent of this embodiment of the present invention is a filter. Examples include, but are not limited to, finite impulse response filters and infinite impulse response filters. In one embodiment, a high-pass $5^{th}$ order filter such as, but not limited to, a Butterworth filter, with a cut-off frequency of 90 Hz is applied to the signal from the reference microphone. This process removes low frequency noise which is not of interest in heart sound analysis.

Further, most noise in the clinical setting appears as a narrowband signal buried in broadband noise. Accordingly, the second component of this embodiment of the present invention is a means for enhancing the narrowband components in the reference signal and facilitating identification of noisy segments. In one embodiment, such means is a computer which uses spectral subtraction for signal enhancement. Alternatively, such means may use a statistical model-based method (logMMSE) or a Wiener filtering method.

In one embodiment, Berouti's method for spectral subtraction which requires an estimate of the noise to be subtracted for the attenuation of broadband noise is used (Berouti et al. "Enhancement of speech corrupted by acoustic noise," in Acoustics, Speech and Signal Processing, IEEE International Conference on ICASSP '79., vol. 4, April 1979, pp. 208-211). For estimating this noise, the component may use, for example, Stahl's method (Stahl et al. "Quantile based noise estimation for spectral subtraction and wiener filtering," in Acoustics, Speech and Signal Processing, 2000 ICASSP '00. IEEE International Conference on, vol. 3, 2000, pp. 1875-1878). As will be understood by the skilled artisan upon reading this disclosure, however, alternative known methods for signal enhancement, such as, but not limited to, minimum controlled recursive averaging (MRCA) and MRCA II can be used.

In another embodiment, logMMSE with MRCA is used to enhance the reference signal.

The enhanced signal is segmented, for example by division into non-overlapping segments, and the short-term log variance (STLV) of each segment is calculated via a means such as the computer system.

Potential noisy segments are then identified by applying a threshold to the STLV signal via a means such as the computer system. In one nonlimiting embodiment, a histogram method is used to estimate a threshold. The method exploits the observation that, after spectral subtraction, STLVs of noisy-free segments aggregate into the peak of an exponential distribution, whereas the STLVs of noisy segments disperse into its tail. This subcomponent selects the threshold as the center value of the right adjacent bin to the peak bin in the histogram. Such exponential redistribution after signal enhancement, however, only occurs when a record contains both noise and noise-free segments. For a record that is primarily noise-free, a redistribution of STLVs is not found after signal enhancement. In this case, the subcomponent assumes that the noisy segments have STLVs more than three standard deviations from the mean. As will be understood by the skilled artisan upon reading this disclosure, however, alternative known methods for estimating the noise input can be used.

The next step of this embodiment of the present invention involves determining if the segments identified as noisy in step 1 have a deleterious influence on the data recorded by the active microphone or microphones. After identifying potential noisy segments via a means such as a computer, it is then determined if the active channels have similar activity during the same period. Since the frequency characteristics of the active and reference channel are not similar, this step cannot use direct cross-correlation between the two channels to verify if the noise activity detected in the reference channel is also present in the active channel. To resolve this difference in frequency characteristics between the active and reference microphone, this step uses an adaptive filter to match the frequency response of the channels before performing cross-correlation. The reference input to the adaptive filter is first high-pass filtered at 90 Hz using, for example, a $5^{th}$ order Butterworth filter. The inputs into the adaptive filter are the high-pass filtered reference segments identified as noisy in step 1 and the corresponding signal segments from the active channel. In one embodiment, a least mean squared (LMS) algorithm is used for adaptive filtering. For the adaptive filtering parameters, this step optimizes the filter length and adaptation coefficient to maximize the cross-correlation between inputs to the adaptive filter. After the adaptive filter has matched the frequency response of the active and reference channel, a threshold is applied to the normalized cross-correlation values of the potential noisy segments via a means such as a computer. Correlations above this threshold are classified as true noisy segments. For true noise, the normalized cross-correlation is usually greater than 0.95.

Once the deleterious noise segments are identified, the final step involves their removal from the active channels by setting the active signal within these segments to zero. Subsequent signal processing algorithms used for detection of CAD will identify these zeroed segments and ignore them.

The above-described automated system embodiment can be used with any clinically useful device that uses heart sounds to perform or aid in diagnosis.

Having thus described the invention in detail, it is to be understood that the foregoing description is not intended to limit the spirit and scope thereof.

What is claimed is:

1. A system for acoustic detection of coronary artery disease and automated editing of heart sound data, said system comprising: a transducer for detecting acoustic heart signals; one or more reference microphones for detecting external and internal noises; a filter with a cutoff frequency of 90 Hz applied to a signal from the one or more reference microphones; an adaptive filter which matches and cross correlates frequency responses of the transducer signal and the signal of the one or more reference microphones; and one or more computers connected to the transducer and reference microphones which executes software for detecting coronary artery disease by processing the detected acoustic heart signals and which serves as a means for enhancing narrowband components in the signal from the one or more reference microphones, for dividing the enhanced signal into non-overlapping segments and calculating log-variance of each segment, for applying a threshold value to potential noisy segments, and for removal of deleterious noise segments from the transducer signal.

2. The system of claim 1 wherein said means for enhancing narrowband components in the signal from the one or more reference microphones comprises spectral subtraction, a statistical model-based method (log MMSE) or a Wiener filtering method.

3. The system of claim 2 wherein said means for enhancing narrowband components further comprises a mean for estimating noise.

4. The system of claim 3 wherein said means for estimating noise comprises Stahl's method, minimum controlled recursive averaging (MRCA) or MRCA II.

5. The system of claim 1 wherein a least mean squared algorithm is used for adaptive filtering.

6. The system of claim 1 wherein the cross-correlated threshold value for a noise segment to be removed is greater than 0.95.

7. A method for acoustic detection of coronary artery disease using the system of claim 1, said method comprising detecting an acoustic heart signal with the transducer; detecting external and internal noises with the reference microphone; and automatically editing the detected acoustic heart signal to remove noisy segments from the detected external and internal noises.

8. A method for reducing noise in an acoustic coronary artery detection system, comprising the steps of: acquiring an acoustic heart signal using a first transducer positioned near a heart; acquiring a reference signal using one or more reference microphones, the reference signal including a noise component; processing the reference signal with an adaptive filter to produce a processed noise signal; removing noise from the acoustic heart signal by subtracting the processed noise signal from the acoustic heart signal; enhancing narrowband components in the reference signal to facilitate identification of noisy segments; and dividing the enhanced signal into non-overlapping segments, calculating log-variance of each segment and applying a threshold to each segment to identify noisy segments for removal.

9. The method of claim 8 further comprising applying a filter with a cut-off frequency of 90 Hz to the reference signal.

* * * * *